(12) United States Patent
Gou

(10) Patent No.: US 10,863,942 B2
(45) Date of Patent: Dec. 15, 2020

(54) MAGNETIC RESONANCE IMAGING DEVICE AND DEMENTIA MONITORING SYSTEM

(71) Applicant: HON HAI PRECISION INDUSTRY CO., LTD., New Taipei (TW)

(72) Inventor: Tai-Ming Gou, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 323 days.

(21) Appl. No.: 16/015,516

(22) Filed: Jun. 22, 2018

(65) Prior Publication Data

US 2019/0261911 A1 Aug. 29, 2019

Related U.S. Application Data

(60) Provisional application No. 62/635,562, filed on Feb. 27, 2018.

(51) Int. Cl.
*A61B 5/05* (2006.01)
*A61B 5/00* (2006.01)
(Continued)

(52) U.S. Cl.
CPC ............ *A61B 5/4088* (2013.01); *A61B 5/002* (2013.01); *A61B 5/0022* (2013.01); *A61B 5/0042* (2013.01); *A61B 5/0555* (2013.01); *A61B 5/7282* (2013.01); *G06T 7/0016* (2013.01); *G06T 2207/10088* (2013.01); *G06T 2207/30016* (2013.01)

(58) Field of Classification Search
None
See application file for complete search history.

(56) References Cited

U.S. PATENT DOCUMENTS

2004/0232916 A1* 11/2004 Kamimura ........... A61B 5/0555
324/318
2005/0187459 A1 8/2005 Trequattrini et al.
(Continued)

FOREIGN PATENT DOCUMENTS

| CN | 1914515 | 2/2007 |
|---|---|---|
| CN | 104094131 | 10/2014 |
| TW | M411221 | 9/2011 |

*Primary Examiner* — Joel F Brutus
(74) *Attorney, Agent, or Firm* — ScienBiziP, P.C.

(57) ABSTRACT

This disclosure relates to a magnetic resonance imaging device. The magnetic resonance imaging device includes an carrying unit; an imaging unit, a controlling computer, and a signal processing computer. The signal processing computer includes a controlling module, a data processing module, an image reconstructing module, an image storing module, and an image comparing module. The image reconstructing module forms cross-sectional scanned images of an user's brain memory showing microstructure. The image comparing module is configured to analyze and compare the cross-sectional scanned images of the user's brain memory showing microstructure captured at different times so that the controlling computer shows different suggestions corresponding to different judgement results of the image comparing module. The system may comprise a dementia monitoring system that provides users with advisory dementia warnings so users may be advised to seek further medical advice.

16 Claims, 7 Drawing Sheets

(51) Int. Cl.
*A61B 5/055* (2006.01)
*G06T 7/00* (2017.01)

(56) References Cited

U.S. PATENT DOCUMENTS

| | | | | |
|---|---|---|---|---|
| 2005/0244036 | A1* | 11/2005 | Rusinek | A61B 5/05 |
| | | | | 382/120 |
| 2006/0260050 | A1* | 11/2006 | Manzione | A61B 6/0457 |
| | | | | 5/601 |
| 2014/0303487 | A1 | 10/2014 | James et al. | |
| 2015/0182143 | A1* | 7/2015 | Hirata | G16H 70/60 |
| | | | | 600/408 |
| 2015/0244665 | A1* | 8/2015 | Choi | H04L 51/24 |
| | | | | 709/206 |
| 2015/0323618 | A1* | 11/2015 | Merfeld | G01R 33/3804 |
| | | | | 324/321 |
| 2016/0155226 | A1* | 6/2016 | Kano | A61B 5/7275 |
| | | | | 382/131 |
| 2018/0011153 | A1* | 1/2018 | Pourrahimi | A61B 5/0555 |

* cited by examiner

MAGNETIC RESONANCE IMAGING DEVICE AND DEMENTIA MONITORING SYSTEM

CROSS-REFERENCE TO RELATED APPLICATIONS

This application claims the benefit under 35 U.S.C. § 119(c) of U.S. Provisional Application No. 62/635,562 filed Feb. 27, 2018, the disclosure of which is incorporated by reference herein.

BACKGROUND

1. Technical Field

The present disclosure relates to medical equipment technical field, especially, relates to magnetic resonance imaging devices and dementia monitoring systems.

2. Description of Related Art

Dementia is a broad category of brain diseases that cause a long-term and often gradual decrease in the ability to think and remember that is great enough to affect a person's daily functioning. Dementia is usually translated as "Shizhizheng" in Taiwan, translated as "Chidaizheng" in Chinese Mainland, and translated as "Tuihuazheng" in Hong Kong. Recently, more and more people suffer a dementia. However, after the patient has been found himself suffer a dementia it can be too late for the patient to receive a treatment.

Therefore, what is needed is equipment for people to detect and predict the dementia so that the patient can go to see a doctor and receive immediate treatment.

BRIEF DESCRIPTION OF THE DRAWINGS

Many aspects of the embodiments can be better understood with reference to the following drawings. The components in the drawings are not necessarily drawn to scale, the emphasis instead being location upon clearly illustrating the principles of the embodiments. Moreover, in the drawings, like reference numerals designate corresponding parts throughout the several views.

DETAILED DESCRIPTION

Figure 1:
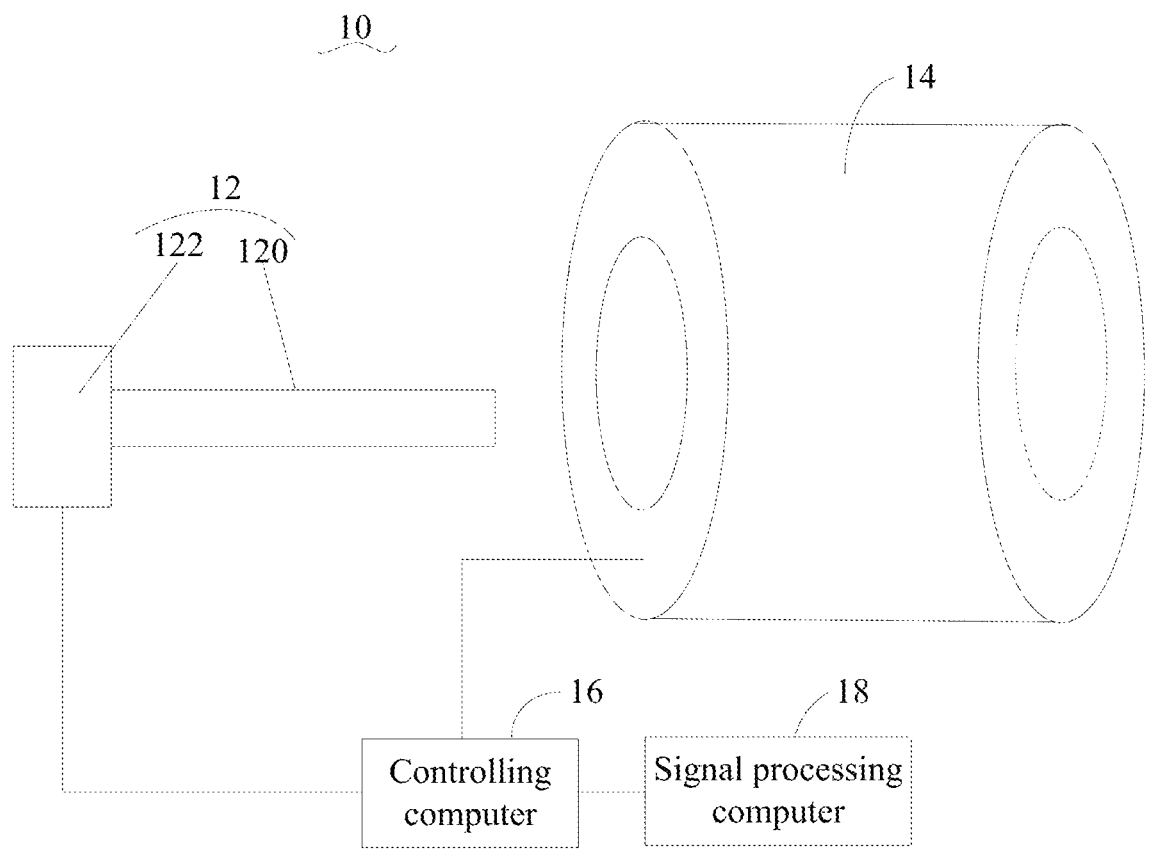
FIG. 1 is a schematic view of one embodiment of a magnetic resonance imaging device.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. The drawings are not necessarily to scale, and the proportions of certain parts may be exaggerated better illustrate details and features. The description is not to considered as limiting the scope of the embodiments described herein.

Several definitions that apply throughout this disclosure will now be presented. The term "coupled" is defined as connected, whether directly or indirectly through intervening components, and is not necessarily limited to physical connections. The connection can be such that the objects are permanently connected or releasably connected. The term "outside" refers to a region that is beyond the outermost confines of a physical object. The term "inside" indicates that at least a portion of a region is partially contained within a boundary formed by the object. The term "substantially" is defined to essentially conforming to the particular dimension, shape or other word that substantially modifies, such that the component need not be exact. For example, substantially cylindrical means that the object resembles a cylinder, but can have one or more deviations from a true cylinder. The term "comprising" means "including, but not necessarily limited to"; it specifically indicates open-ended inclusion or membership in a so-described combination, group, series and the like. It should be noted that references to "an" or "one" embodiment in this disclosure are not necessarily to the same embodiment, and such references mean at least one.

In general, the word "module," as used herein, refers to logic embodied in hardware or firmware, or to a capturing of software instructions, written in a programming language, such as, for example, Java, C, or assembly. One or more software instructions in the modules may be embedded in firmware, such as an EPROM. It will be appreciated that modules may comprise connected logic units, such as gates and flip-flops, and may comprise programmable units, such as programmable gate arrays or processors. The modules described herein may be implemented as either software and/or hardware modules and may be stored in any type of computer-readable medium or other computer storage device.

References will now be made to the drawings to describe, in detail, various embodiments of the present magnetic resonance imaging devices and dementia monitoring systems.

Embodiment 1

Referring to FIG. 1, a magnetic resonance imaging device 10 of embodiment 1 is provided. The magnetic resonance imaging device 10 includes a carrying unit 12, an imaging unit 14, a controlling computer 16, and a signal processing computer 18.

The carrying unit 12 includes a rotatable bed 120, and a bed rotator 122. The rotatable bed 120 supports the user and transport the user into the detecting magnetic field generated by the imaging unit 14. The bed rotator 122 rotates the rotatable bed 120 so that the user can be rotated 360 degrees. The imaging unit 14 can capture the cross-sectional scanned image of the brain memory showing microstructure at different angles by rotating the user. Because the carrying unit 12 includes the bed rotator 122, the imaging unit 14 need not have a rotatable scanning device. Thus, the imaging unit 14 can have smaller volume and simple structure so that the magnetic resonance imaging device 10 can be used in a location other than a hospital.

The imaging unit 14 includes a magnet assembly (not shown) and a magnetic resonance spectroscopy (not shown). The magnet assembly includes a main magnet (not shown), a compensative coil (not shown), a gradient coil (not shown), and a radio frequency coil (not shown). The main magnet produces strong static magnetic field, the compensative coil makes the static magnetic field approach the ideal uniform magnetic field, the gradient coil produces a gradient magnetic field, and the radio frequency coil produces a radiofrequency magnetic field. The magnetic resonance spectroscopy includes a frequency transmitting unit (not shown) and a magnetic resonance signal receiving system (not shown). The magnetic resonance signal receiving system converts the magnetic resonance signal to a digital signal by a convertor, stores the digital signal in a register or sends the digital signal to the signal processing computer 18.

The controlling computer 16 controls the operation of the magnetic resonance imaging device 10. The controlling computer 16 can include a user interface (not shown) so that the user can operate the magnetic resonance imaging device 10. The controlling computer 16 can also be connected to the mobile electronic device (not shown) of the user, such as mobile phone, by wires or wireless. Thus, the user can operate the magnetic resonance imaging device 10 by downloading an APP on the mobile phone.

Figure 2:
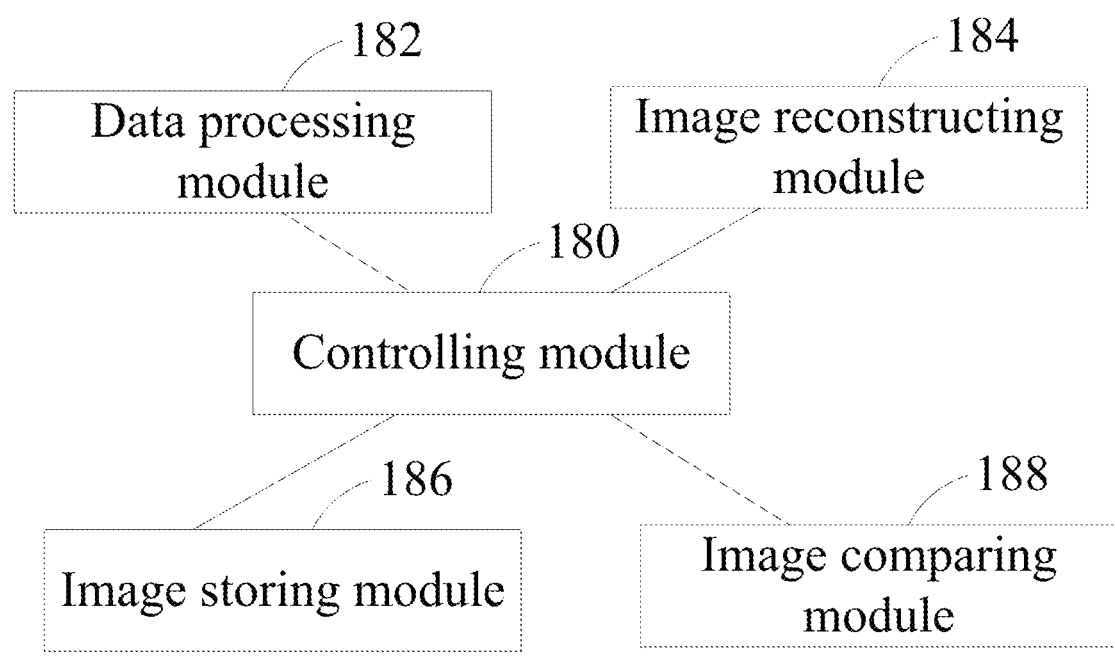
FIG. 2 is a function block diagram of one embodiment of a signal processing computer of the magnetic resonance imaging device.

Referring to FIG. 2, in one embodiment, the signal processing computer 18 includes a controlling module 180, a data processing module 182, an image reconstructing module 184, an image storing module 186, and an image comparing module 188. The controlling module 180 is respectively electrically connected to and controls the work of the data processing module 182, the image reconstructing module 184, the image storing module 186, and the image comparing module 188. The data processing module 182 processes the raw data to form a processed data. The image reconstructing module 184 forms magnetic resonance images with different parameters according to the processed data. The image storing module 186 stores the magnetic resonance images. The magnetic resonance images are cross-sectional scanned images of the user's brain memory showing microstructure. The image comparing module 188 analyzes and compare the cross-sectional scanned images of the user's brain memory showing microstructure captured at different times. The controlling computer 16 can output different suggestions, that corresponding to different judgement results of the image comparing module 188, to the user.

In one embodiment, the judgement results of the image comparing module 188 includes three changes levels. Level 1: the cross-sectional scanned images of the user's brain memory showing microstructure captured at different times have no changes. Level 2: the cross-sectional scanned images of the user's brain memory showing microstructure captured at different times have slight changes. Level 3: the cross-sectional scanned images of the user's brain memory showing microstructure captured at different times have obvious changes. The "no changes", "slight changes", and "obvious changes" are determined according to the size changes of the cross-sectional scanned images along a single direction or several different directions. In one embodiment, H1 is defined as a first changes threshold, H2 is defined as a second changes threshold, and H1<H2. When the changes of the cross-sectional scanned images is less than the first changes threshold H1, the judgement is "no changes." When the changes of the cross-sectional scanned images is greater than or equal to the first changes threshold H1 and less than or equal to the second changes threshold H2, the judgement is "slight changes." When the changes of the cross-sectional scanned images is greater than the second changes threshold H2, the judgement is "obvious changes." The first changes threshold H1 and the second changes threshold H2 can be set according to the actual situation. The first changes threshold H1 and the second changes threshold H2 can be a length value or a rate. For example, the first changes threshold H1 is 2-5%, and the second changes threshold H2 is 5%-10%. Namely, the first changes threshold H1 and the second changes threshold H2 are reduction rate. In one embodiment, the size $L_n$ of the cross-sectional scanned image captured in the $n^{th}$ time is compared with the size $L1$ of the cross-sectional scanned image captured in the first time, "n" is an integer greater than 1. For example, when the condition $(L1-L_n)/L_n<2\%$ is met, the judgement is "no changes"; when the condition $2\%<(L1-L_n)/L_n<5\%$ is met, the judgement is "slight changes"; when the condition $5\%<(L1-L_n)/L_n$ is met, the judgement is "obvious changes." The size $L_n$ can be a length or width along any direction.

The controlling computer 16 can output different suggestions to the user corresponding to different judgement results of the image comparing module 188. The outputted suggestions can be designed as needed. For example, when the cross-sectional scanned images of the user's brain memory showing microstructure captured at different times have no changes, the outputted suggestion is "You do not have evidence of dementia"; when the cross-sectional scanned images of the user's brain memory showing microstructure captured at different times have slight changes, the outputted suggestion is "You may have dementia, please consult a doctor"; and when the cross-sectional scanned images of the user's brain memory showing microstructure captured at different times have obvious changes, the outputted suggestion is "You appear to have evidence of dementia, please see a doctor immediately." The device should also warn the user that it is not providing medical advice, but merely reacting to certain changes in the user's brain structure, etc.

Figure 3:
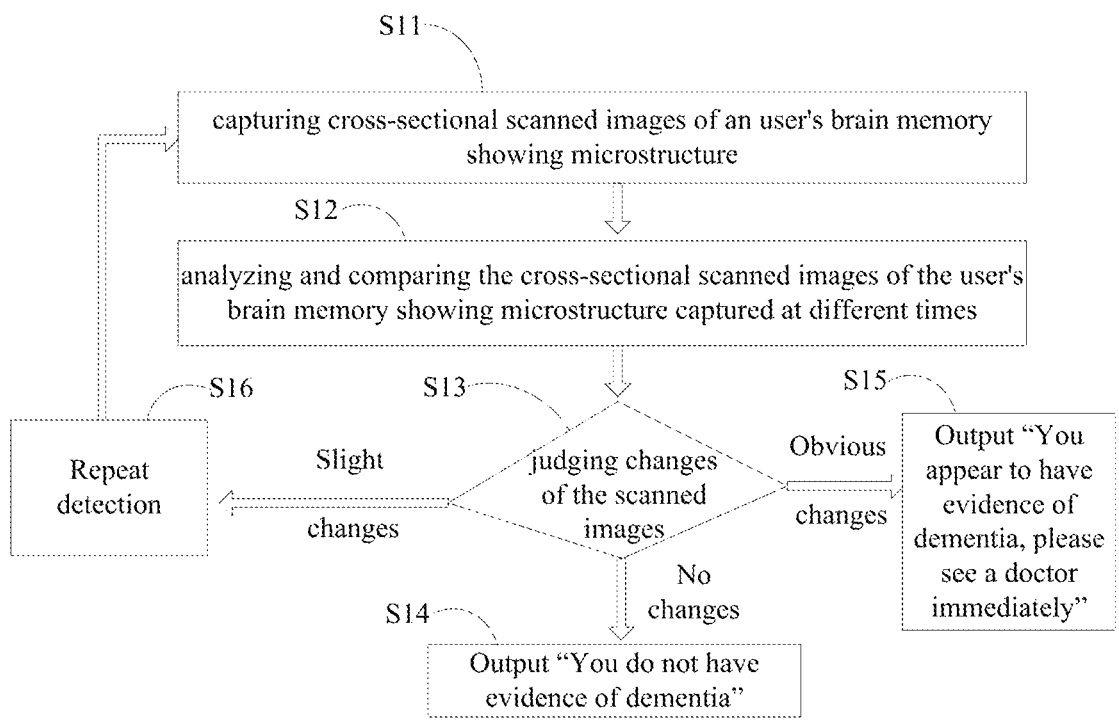
FIG. 3 is a work flow chart of one embodiment of the magnetic resonance imaging device.

Referring to FIG. 3, alternatively, when the cross-sectional scanned images of the user's brain memory showing microstructure captured at different times have slight changes, the magnetic resonance imaging device 10 can repeat detection. The work method of the magnetic resonance imaging device 10 includes following steps:

step (S11), capturing cross-sectional scanned images of an user's brain memory showing microstructure;

step (S12), analyzing and comparing the cross-sectional scanned images of the user's brain memory showing microstructure captured at different times;

step (S13), judging changes of the cross-sectional scanned images, when the judgement is "no changes", go to step (S14), when the judgement is "obvious changes" go to step (S15); when the judgement is "slight changes", go to step (S16);

step (S14), output "You do not have evidence of dementia";

step (S15), output "You appear to have evidence of dementia, please see a doctor immediately"; and step (S16), repeat detection.

In step (S16), when the judgement is still "slight changes" after repeating detection three times, output "You may have dementia, please see a doctor immediately."

Because the dementia may cause the brain memory reduction along any one or more than one directions, the several size Ln along different directions can be used to judge the changes level so that to have an accurate judgement. In one embodiment, the maximum of the changes along different directions of the cross-sectional scanned images is compared with the first changes threshold H1 and the second changes threshold H2, thus the accuracy is improved.

In one embodiment, a plurality of first lengths Lnx along X direction, a plurality of second lengths Lny along Y direction, and a plurality of third lengths Lnz along Z direction, of the cross-sectional scanned image of the user's brain memory showing microstructure are captured. The X direction, the Y direction, and the Z direction are perpendicular with each other. The image comparing module 188 analyzes and compares the cross-sectional scanned images of the user's brain memory showing microstructure by respectively using the first lengths Lnx, the second lengths Lny, and the third lengths Lnz. Thus, a first judgement result along X direction, a second judgement result along Y direction, and a third judgement result along Z direction are obtained. If the three directions have the same judgement result, the same judgement result is used as the final judgement. If any two directions have the same judgement result, the same judgement result of the two directions is used as the final judgement. If the three directions have different judgement results, "slight changes" is used as the final judgement.

Figure 4:
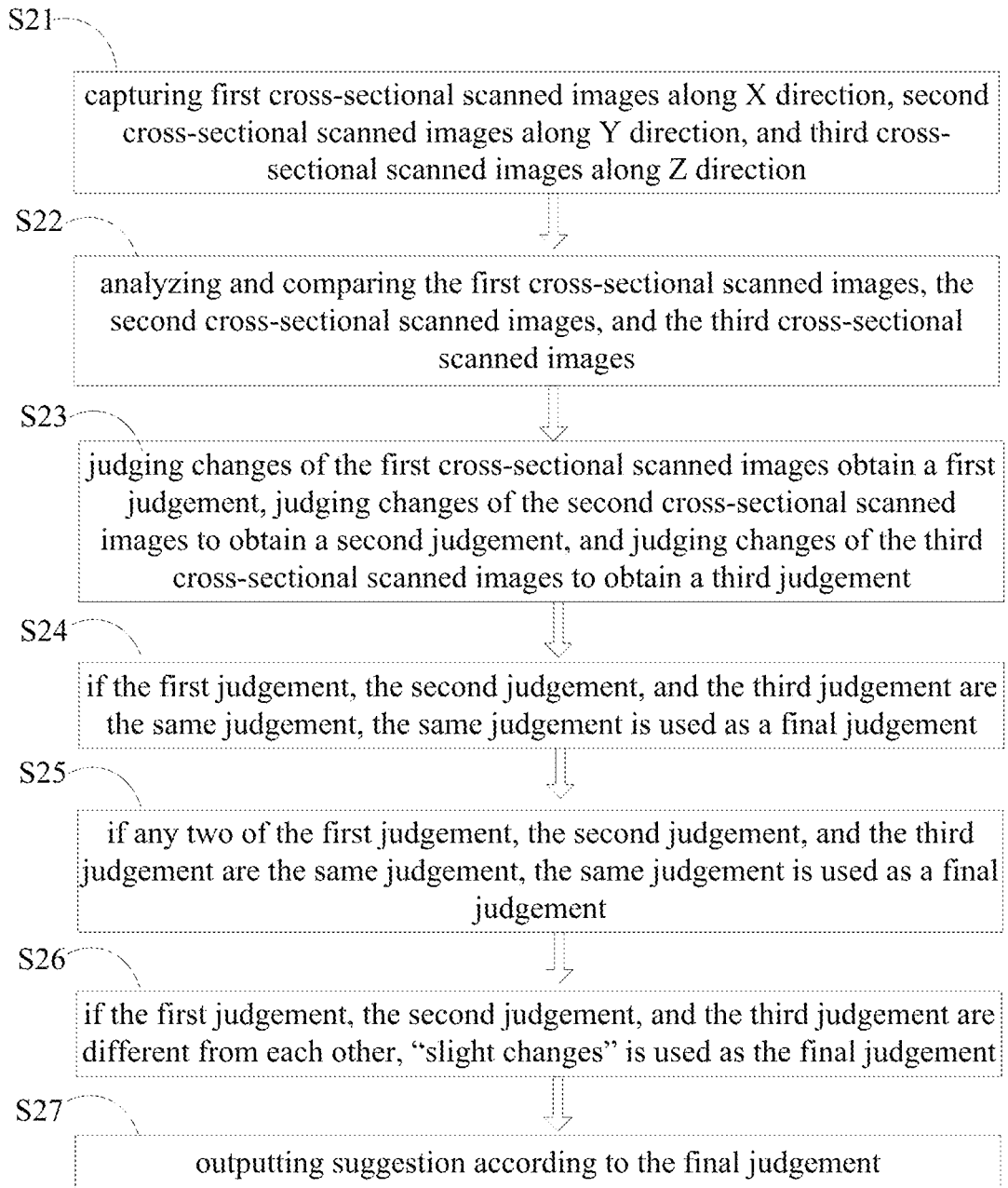
FIG. 4 is a work flow chart of another embodiment of the magnetic resonance imaging device.

Referring to FIG. 4, in one embodiment, the work method of the magnetic resonance imaging device 10 includes following steps:

step (S21), capturing first cross-sectional scanned images along X direction, second cross-sectional scanned images along Y direction, and third cross-sectional scanned images along Z direction;

step (S22), analyzing and comparing the first cross-sectional scanned images, the second cross-sectional scanned images, and the third cross-sectional scanned images;

step (S23), judging changes of the first cross-sectional scanned images obtain a first judgement, judging changes of the second cross-sectional scanned images to obtain a second judgement, and judging changes of the third cross-sectional scanned images to obtain a third judgement;

step (S24), if the first judgement, the second judgement, and the third judgement are the same judgement, the same judgement is used as a final judgement;

step (S25), if any two of the first judgement, the second judgement, and the third judgement are the same judgement, the same judgement is used as a final judgement;

step (S26), if the first judgement, the second judgement, and the third judgement are different from each other, "slight changes" is used as the final judgement; and step (S27), outputting suggestion according to the final judgement.

In steps (S27), when the final judgement is "no changes", the suggestion is "You do not have evidence of dementia"; when the final judgement is "obvious changes", the suggestion is "You appear to have evidence of dementia, please see a doctor immediately"; when the final judgement is "slight changes", the suggestion is "repeat detection."

In another embodiment, the magnetic resonance imaging device 10 has a fast detecting mode and an accurate detecting mode. In the fast detecting mode, only the lengths Ln along a single direction are obtained and used to judge the dementia. In the accurate detecting mode, the plurality of first lengths Lnx along X direction, the plurality of second lengths Lny along Y direction, and the plurality of third lengths Lnz along Z direction are obtained to used judge the dementia. The user can select the work mode of the magnetic resonance imaging device 10 as needed.

The magnetic resonance imaging device 10 can be installed in a public location, such as a mall or a cafe. The new user can register an account as an ID and login each time. The user can go to the nearest magnetic resonance imaging device 10 to take an examination. The user can operate the magnetic resonance imaging device 10 by a mobile phone that is connected to the magnetic resonance imaging device 10 by wire or wireless. For example, the user can operate the magnetic resonance imaging device 10 by scanning the quick response code by the mobile phone. The magnetic resonance imaging device 10 can send the suggestion to the mobile phone. The user are also reminded that the test results are only suggestions and not medical advice.

Embodiment 2

Figure 5:
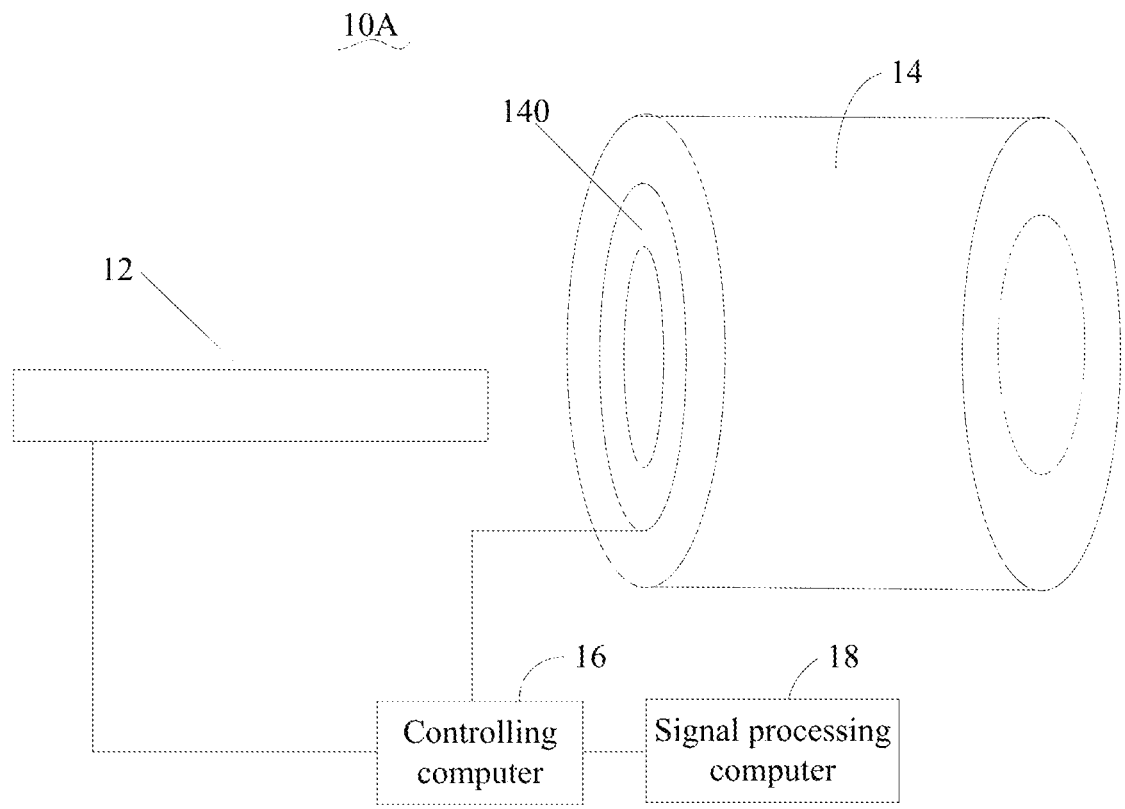
FIG. 5 is a schematic view of another one embodiment of a magnetic resonance imaging device.

Referring to FIG. 5, a magnetic resonance imaging device 10A of embodiment 2 is provided. The magnetic resonance imaging device 10A includes an carrying unit 12, an imaging unit 14, a controlling computer 16, and a signal processing computer 18.

The magnetic resonance imaging device 10A of embodiment 2 is similar to the magnetic resonance imaging device 10 of embodiment 1, except that the rotatable bed 120 of the carrying unit 12 is not rotatable, and the imaging unit 14 includes a rotatable scanning device 140. The rotatable scanning device 140 can changes the gradient direction of the gradient magnetic field and the magnetic field direction of the radiofrequency magnetic field so that the user can be scanned from different angles.

Embodiment 3

Figure 6:
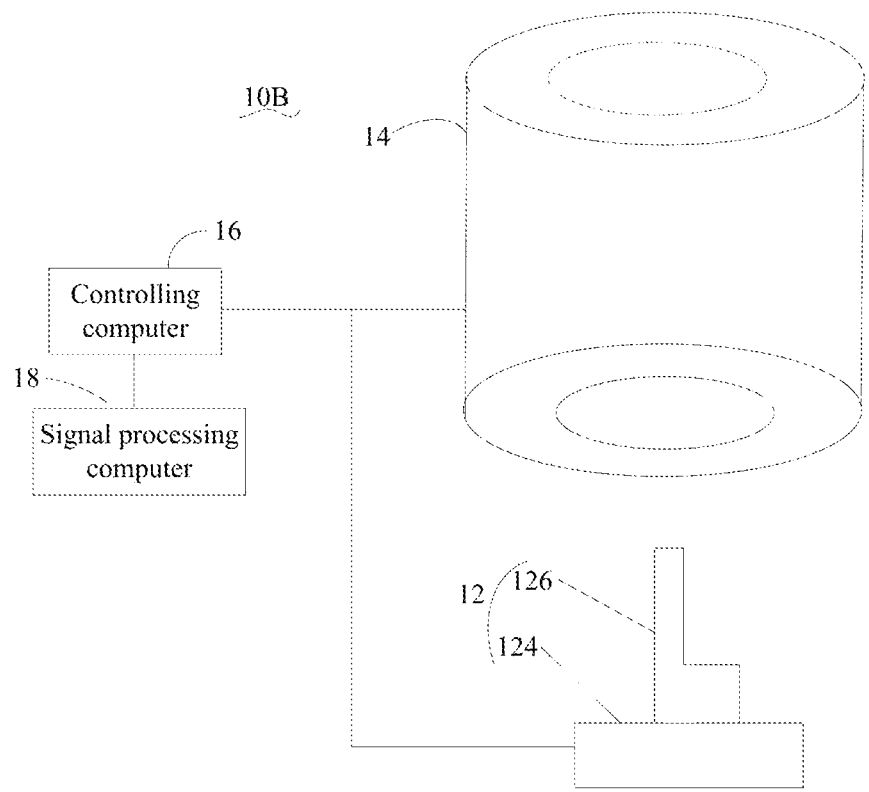
FIG. 6 is a schematic view of another one embodiment of a magnetic resonance imaging device.

Referring to FIG. 6, a magnetic resonance imaging device 10B of embodiment 3 is provided. The magnetic resonance imaging device 10B includes an carrying unit 12, an imaging unit 14, a controlling computer 16, and a signal processing computer 18.

The magnetic resonance imaging device 10B of embodiment 3 is similar to the magnetic resonance imaging device 10 of embodiment 1, except that the imaging unit 14 is suspended, and the carrying unit 12 includes a rotatable elevating platform 124 and a user support 126 located on the rotatable elevating platform 124. The user support 126 can be a chair. In one embodiment, the imaging unit 14 is suspended by hanging from a roof. In operation, the user can stand on the rotatable elevating platform 124 or sit on the chair, and the rotatable elevating platform 124 lifts the user into the detecting magnetic field. Since the magnetic resonance imaging device 10B is only use to detect the head of the user, only the upper part of the body needs to be moved into the room defined by the imaging unit 14. The user can stand or sit in the detecting process. Because the imaging unit 14 of the magnetic resonance imaging device 10B is suspended, floor space is saved. The user can have a better experience in the rotating process by standing or sitting than by lying as in embodiment 1.

Embodiment 4

Figure 7:
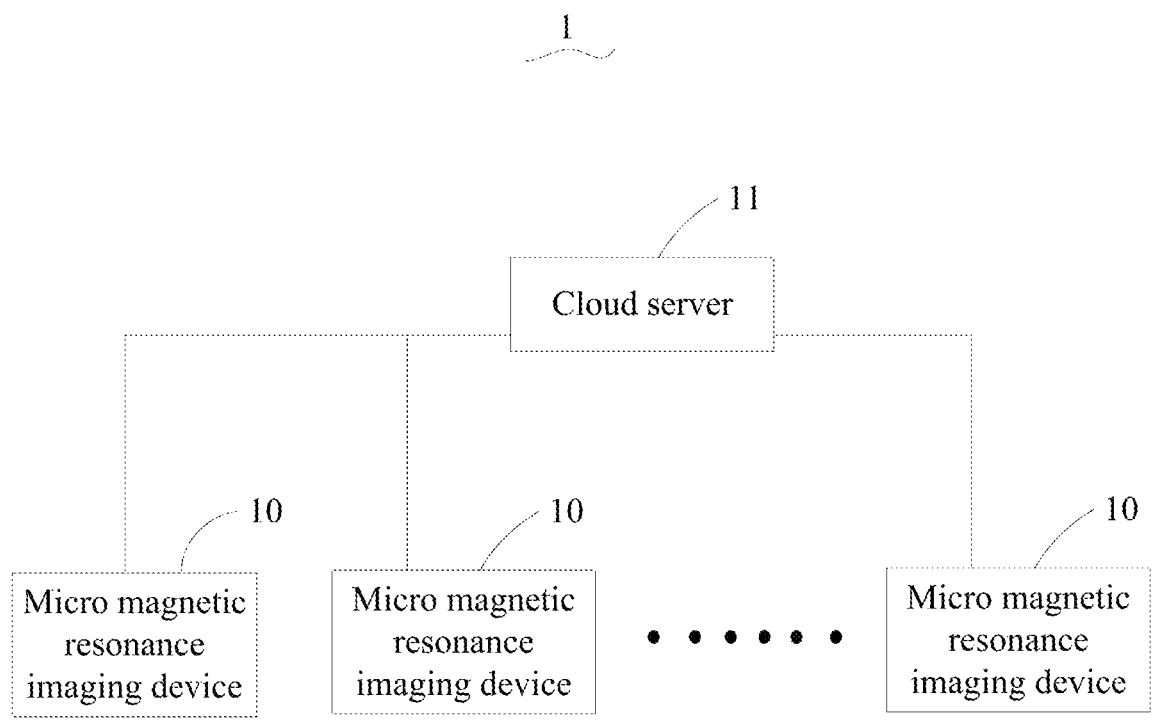
FIG. 7 is a function block diagram of one embodiment of a dementia monitoring system using the magnetic resonance imaging devices above.

Referring to FIG. 7, a dementia monitoring system 1 of embodiment 4 is provided. The dementia monitoring system 1 includes a plurality of magnetic resonance imaging devices 10 located in different locations and a cloud server 11 electrically connected to the plurality of magnetic resonance imaging devices 10 by wires or wireless. The plurality of magnetic resonance imaging devices 10 is configures to capture cross-sectional scanned images of an user's brain memory showing microstructure and send the cross-sectional scanned images to the cloud server 11. The cloud server 11 is configures to store, analysis, and compare the cross-sectional scanned images of the user's brain memory showing microstructure captured at different times. The cloud server 11 also sends the judgement results to the mobile electronic devices such as mobile phone.

The dementia monitoring system 1 allows the user to select the nearest magnetic resonance imaging device 10 for imaging, so that the user does not have to always go to the same location. The magnetic resonance imaging device 10 can also be replaced by the magnetic resonance imaging devices 10A, 10B.

Alternatively, because the cloud server 11 plays the functions of analyzing and comparing the cross-sectional scanned images, each of the plurality of magnetic resonance imaging devices 10 can only include the carrying unit 12, the imaging unit 14, and the controlling computer 16 and have not any signal processing computer 18.

It is to be understood that the above-described embodiments are intended to illustrate other than limit the disclosure. Any elements described in accordance with any embodiments is understood that they can be used in addition or substituted in other embodiments. Embodiments can also be used together. Variations may be made to the embodiments without departing from the spirit of the disclosure. The above-described embodiments illustrate the scope of the disclosure but do not restrict the scope of the disclosure.

Depending on the embodiment, certain of the steps of methods described may be removed, others may be added, and the sequence of steps may be altered. It is also to be understood that the description and the claims drawn to a method may include some indication in reference to certain steps. However, the indication used is only to be viewed for identification purposes and not as a suggestion as to an order for the steps.

What is claimed is:

1. A magnetic resonance imaging device, comprising:
   a carrying unit;
   an imaging unit;
   a controlling computer; and
   a signal processing computer, the signal processing computer comprises a controlling module, a data processing module, an image reconstructing module, and an image storing module; and the image reconstructing module form cross-sectional scanned images of an user's brain memory showing microstructure;
   wherein the signal processing computer further comprises an image comparing module, the image comparing module is configured to analyze and compare size changes of the cross-sectional scanned images of the user's brain memory showing microstructure along a single direction or several different directions captured at different times, and the controlling computer shows different suggestions corresponding to different judgement results of the image comparing module; H1 is defined as a first changes threshold, H2 is defined as a second changes threshold, and H1<H2, the first changes threshold H1 and the second changes threshold H2 are reduction rate, a size Ln of the cross-sectional scanned image captured in the $n^{th}$ time is compared with a size L1 of the cross-sectional scanned image captured in the first time, and "n" is an integer greater than 1, the judgement results comprises at least three changes levels, namely:
   the changes of the cross-sectional scanned images captured at different times is less than the first changes threshold H1, and (L1−Ln)/Ln<2%; the cross-sectional scanned images of the user's brain memory showing microstructure captured at different times have no changes;
   the changes of the cross-sectional scanned images captured at different times is greater than or equal to the first changes threshold H1 and less than or equal to the second changes threshold H2, and 2%<(L1−Ln)/Ln<5%; the cross-sectional scanned images of the user's brain memory showing microstructure captured at different times have slight changes; and
   the changes of the cross-sectional scanned images captured at different times is greater than the second changes threshold H2, and 5%<(L1−Ln)/Ln; the cross-sectional scanned images of the user's brain memory showing microstructure captured at different times have changes.

2. The magnetic resonance imaging device as claimed in claim 1, wherein the carrying unit comprises a rotatable bed and a bed rotator, and the bed rotator is configured to rotate the rotatable bed 360 degrees.

3. The magnetic resonance imaging device as claimed in claim 1, wherein the imaging unit further comprises a rotatable scanning device, the rotatable scanning device is configured to changes a gradient direction of a gradient magnetic field and a direction of a radiofrequency magnetic field so that the user is scanned from different angles.

4. The magnetic resonance imaging device as claimed in claim 1, wherein the imaging unit is suspended, and the carrying unit comprises a rotatable elevating platform and a user support located on the rotatable elevating platform.

5. The magnetic resonance imaging device as claimed in claim 1, wherein the controlling computer comprises a user interface.

6. The magnetic resonance imaging device as claimed in claim 1, wherein the controlling computer is to be connected to a mobile electronic device of the user, whereby a user operates the magnetic resonance imaging device by downloading and using an application.

7. The magnetic resonance imaging device as claimed in claim 1, wherein a work method of the magnetic resonance imaging device comprises:
   step (S11), capturing cross-sectional scanned images of the user's brain memory showing microstructure;
   step (S12), analyzing and comparing the cross-sectional scanned images of the user's brain memory showing microstructure captured at different times; and
   step (S13), judging changes of the cross-sectional scanned images and outputting a suggestion according to the changes of the cross-sectional images.

8. The magnetic resonance imaging device as claimed in claim 7, wherein the work method of the magnetic resonance imaging device comprises:
   capturing first cross-sectional scanned images along X direction, second cross-sectional scanned images along Y direction, and third cross-sectional scanned images along Z direction;
   analyzing and comparing the first cross-sectional scanned images, the second cross-sectional scanned images, and the third cross-sectional scanned images;
   judging changes of the first cross-sectional scanned images obtain a first judgement, judging changes of the second cross-sectional scanned images to obtain a second judgement, and judging changes of the third cross-sectional scanned images to obtain a third judgement;

obtaining a final judgement by comparing the first judgement, the second judgement, and the third judgement; and outputting suggestion according to the final judgement.

9. A dementia detecting system, comprising:
a plurality of magnetic resonance imaging devices, wherein each of the plurality of magnetic resonance imaging devices comprises:
a carrying unit;
an imaging unit; and
a controlling computer;
a cloud server connected to the plurality of magnetic resonance imaging devices, wherein the cloud server comprises:
a controlling module;
a data processing module;
an image reconstructing module, the image reconstructing module form cross-sectional scanned images of an user's brain memory showing microstructure;
an image storing module; and
an image comparing module, wherein the image comparing module is configured to analyze and compare size changes of the cross-sectional scanned images of the user's brain memory showing microstructure along a single direction or several different directions captured at different times, and the cloud server sends different suggestions, corresponding to different judgement results of the image comparing module, to a mobile electronic device; H1 is defined as a first changes threshold, H2 is defined as a second changes threshold, and H1<H2, the first changes threshold H1 and the second changes threshold H2 are reduction rate, a size Ln of the cross-sectional scanned image captured in the $n^{th}$ time is compared with a size L1 of the cross-sectional scanned image captured in the first time, and "n" is an integer greater than 1, the judgement results comprises at least three changes levels, namely:
the changes of the cross-sectional scanned images captured at different times is less than the first changes threshold H1, and (L1−Ln)/Ln<2%; the cross-sectional scanned images of the user's brain memory showing microstructure captured at different times have no changes;
the changes of the cross-sectional scanned images captured at different times is greater than or equal to the first changes threshold H1 and less than or equal to the second changes threshold H2, and 2%<(L1−Ln)/Ln<5%; the cross-sectional scanned images of the user's brain memory showing microstructure captured at different times have slight changes; and
the changes of the cross-sectional scanned images captured at different times is greater than the second changes threshold H2, and 5%<(L1−Ln)/Ln; the cross-sectional scanned images of the user's brain memory showing microstructure captured at different times have changes.

10. The dementia monitoring system as claimed in claim 9, wherein the carrying unit comprises a rotatable bed and a bed rotator, and the bed rotator is configured to rotate the rotatable bed 360 degrees.

11. The dementia monitoring system as claimed in claim 9, wherein the imaging unit further comprises a rotatable scanning device, the rotatable scanning device is configured to changes a gradient direction of a gradient magnetic field and a direction of a radiofrequency magnetic field so that the user is scanned from different angles.

12. The dementia monitoring system as claimed in claim 9, wherein the imaging unit is suspended, and the carrying unit comprises a rotatable elevating platform and a user support located on the rotatable elevating platform.

13. The dementia monitoring system as claimed in claim 9, wherein the controlling computer comprises a user interface.

14. The dementia monitoring system as claimed in claim 9, wherein the controlling computer is to be connected to the mobile electronic device, so that the user operates the magnetic resonance imaging device by downloading an application.

15. The dementia monitoring system as claimed in claim 9, wherein a work method of the dementia monitoring system comprises:
step (S11), capturing cross-sectional scanned images of the user's brain memory showing microstructure;
step (S12), analyzing and comparing the cross-sectional scanned images of the user's brain memory showing microstructure captured at different times;
step (S13), judging changes of the cross-sectional scanned images and outputting a suggestion to the mobile electronic device according to the changes of the cross-sectional scanned images.

16. The dementia monitoring system as claimed in claim 15, wherein the work method of the dementia monitoring system comprises:
capturing first cross-sectional scanned images along X direction, second cross-sectional scanned images along Y direction, and third cross-sectional scanned images along Z direction;
analyzing and comparing the first cross-sectional scanned images, the second cross-sectional scanned images, and the third cross-sectional scanned images;
judging changes of the first cross-sectional scanned images obtain a first judgement, judging changes of the second cross-sectional scanned images to obtain a second judgement, and judging changes of the third cross-sectional scanned images to obtain a third judgement;
obtaining a final judgement by comparing the first judgement, the second judgement, and the third judgement; and
sending a suggestion according to the final judgement.

* * * * *